United States Patent
Payne et al.

(10) Patent No.: US 6,652,459 B2
(45) Date of Patent: Nov. 25, 2003

(54) OPHTHALMIC USES OF LASERS

(75) Inventors: Peter Alfred Payne, 16 The Stables, Tabley House, Tabley, Cheshire WA16 OHA (GB); Richard James Dewhurst, c/o UMIST, Department of Instrumentation and Analytical Science, P.O. Box 88, Manchester, M60 1QD (GB); Emmanuel Rosen, Manchester (GB); Andrew Fink, c/o UMIST, Department of Instrumentation and Analytical Science, P.O. Box 88, Manchester, M60 1QD (GB); Ali Sadr, Manchester (GB)

(73) Assignees: Peter Alfred Payne, Cheshire (GB); Richard James Dewhurst, Manchester (GB); Emanual Rosen, Manchester (GB); Andrew Fink, Manchester (GB)

( * ) Notice: Subject to any disclaimer, the term of this patent is extended or adjusted under 35 U.S.C. 154(b) by 0 days.

(21) Appl. No.: 09/888,870

(22) Filed: Jun. 25, 2001

(65) Prior Publication Data

US 2002/0097374 A1 Jul. 25, 2002

Related U.S. Application Data

(60) Provisional application No. 60/214,872, filed on Jun. 28, 2000.

(51) Int. Cl.[7] .............................. A61B 8/00; A61B 6/00
(52) U.S. Cl. ................. 600/439; 600/476; 600/452; 600/438; 351/212
(58) Field of Search .................. 600/407–482; 351/201–246

(56) References Cited

U.S. PATENT DOCUMENTS

| | | | | |
|---|---|---|---|---|
| 4,200,399 A | * | 4/1980 | Kimble et al. | 356/437 |
| 4,402,601 A | * | 9/1983 | Riva | 356/28.5 |
| 4,564,018 A | | 1/1986 | Hutchison et al. | |
| 4,633,866 A | * | 1/1987 | Peyman et al. | 606/3 |
| 5,085,220 A | * | 2/1992 | Nudell et al. | 600/455 |
| 5,305,759 A | * | 4/1994 | Kaneko et al. | 356/318 |
| 5,369,454 A | * | 11/1994 | Reinstein et al. | 351/201 |
| 5,521,657 A | * | 5/1996 | Klopotek | 351/212 |
| 5,728,156 A | * | 3/1998 | Gupta et al. | 623/6.26 |
| 6,179,421 B1 | * | 1/2001 | Pang | 351/205 |
| 6,440,070 B2 | * | 8/2002 | Israel | 600/476 |

FOREIGN PATENT DOCUMENTS

| | | |
|---|---|---|
| EP | 0-282-234 | 3/1988 |
| GB | 2212920 A | 8/1989 |
| GB | 2322941 A | 9/1998 |
| WO | WO94/28804 | 12/1994 |

OTHER PUBLICATIONS

Hee, M. R., Izatt, J. A., Swanson, E. A., Huang, D., Schuman, J. S., Lin, C. P., Puliafito, C. A., and Fujimoto, J. G., Optical Coherence Tomography for Ophthalmic Imaging, IEEE Engineering in Medicine and Biology, Jan./Feb. 1995, p. 67–76.*

* cited by examiner

Primary Examiner—Francis J. Jaworski
Assistant Examiner—William Jung
(74) Attorney, Agent, or Firm—Wallenstein & Wagner, Ltd.

(57) ABSTRACT

There is disclosed a method for analysis and therapy of the eye utilizing laser-induced ultrasound.

27 Claims, 6 Drawing Sheets

OPHTHALMIC USES OF LASERS

This application claims the benefit of Provisional Application No. 60/214,872 filed Jun. 28, 2000.

TECHNICAL FIELD

This invention relates to ophthalmic uses of lasers, in particular the methods for analysis and therapy of the eye utilising laser induced ultrasound.

BACKGROUND

There is considerable interest in medical applications of ultrasound and photo acoustic waves, sometimes known as laser-generated ultrasonic waves. This is because, in contrast to interrogating techniques such as X-ray imaging and scintigraphy, ultrasound offers the possibility of interrogating a subject with no harmful side effects. Ultrasound imaging of cardiac structures, the vascular systems, the foetus and uterus, abdominal organs such as the liver, kidneys and gall bladder is known. Conventional ultrasound measurements of the eye, using piezoelectric devices to generate ultrasound, are known, and are employed to conduct dimensional measurements of the position of various interfaces within the eye. High resolution measurements are needed for measurements of the front portion of the eye. However, the high frequency ultrasonic signal employed for these measurements do not penetrate the retina and beyond, and hence a lower frequency piezo electric transducer is employed in order to measure these larger dimensions. This has the disadvantage of giving rise to a loss of relative distance information. Additional disadvantages are that two piezoelectric transducers are required, and that separate measurements are necessitated.

SUMMARY OF THE INVENTION

The present invention provides an improved method for analysing an eye using laser radiation to generate ultrasound at desired locations in the eye.

According to the invention there is provided a method for analysis and/or therapy of an eye comprising the step of directing laser radiation into the eye, the characteristics of the laser radiation being suitable to generate ultrasound at desired locations within the eye.

It is possible to generate ultrasound in this way at numerous locations within the eye using a single source. In particular, ultrasound may be generated at the back of the eye, at the sclera, choroid, retina or vitreous humour, or at the front of the eye, i.e. the cornea, lens, iris and ciliary body and the aqueous humour, by a single laser pulse. To reflect ultrasound from the retina requires the use of much lower frequency ultrasound signals than needed to make high resolution dimensional measurements of the front portion of the eye. Conventionally, this necessitates the use of two piezoelectric transducers.

The generated ultrasound may be detected by ultrasonic transducer means connected to the eye by an acoustic coupling medium. The method may comprise an analysis of the eye in which the time taken for the generated ultrasound to propagate from the location at which it is generated to the ultrasonic transducer means, or a time value closely related thereto, is measured, and information concerning the eye is derived therefrom. The information concerning the eye may comprise the spatial dimensions of the eye or of one or more components of the eye. The information concerning the eye may also comprise opacity measurements within the eye.

The laser radiation may be directed to the eye substantially along an axis which is substantially parallel to the optical axis of the lens. The term "substantially along an axis" is intended to encompass instances where a laser beam does not propagate along a single axis due to divergence of the beam or focussing of the beam, but, nonetheless, an "average" beam path is described by a single axis.

Alternatively, the laser radiation may be directed into the eye substantially along an axis which is substantially non-parallel to the optical axis of the lens. This enables inter alia "off axis" White-White measurements to determine the dimensions of the ciliary sulcus.

The point of entry of the laser radiation into the eye may be varied. In this way, an image of the eye, or one or more components of the eye, may be constructed from measurements made at a plurality of points of entry of the laser radiation into the eye. In this way, a B-scan may be performed. The variation of point of entry of the laser radiation—which is preferably accomplished by traversing a laser beam vertically or horizontally across the eye—may be combined with "off-axis" measurements of the type described above.

A plurality of ultrasonic transducers may be employed to provide a plurality of response waveforms, and the waveforms may be processed by adding appropriate time delays thereto so as to provide position sensitive measurements of the generated ultrasound. The laser radiation may emanate from a source, and the plurality of ultrasonic transducers may comprise a plurality of substantially annular transducers arranged substantially concentrically with respect to the source. Alternatively, the plurality of ultrasonic transducers may comprise an array of discrete ultrasonic transducers, and the responsive waveforms provided thereby may be processed to provide a three dimensional image of the eye, or of one or more components of the eye.

Information concerning the lens may be derived from the generated ultrasound, such as the size and position of the lens.

Information concerning light scattering sources present in the eye may be derived from the generated ultrasound.

The opacity of the lens may be measured.

The presence of flare and cells and like scattering sources in the vitreous humour and/or aqueous humour may be detected.

Preferably, a device having ultrasonic transducer means and a source for directing the laser radiation to the eye combined in a single housing is used. Such devices are known from, or may be adapted from devices known from, British Patent Application GB 2 212 920 A and International Publication WO 94/28804, the contents of which are hereby incorporated by reference.

The acoustic coupling medium may comprise a saline solution or a gel.

The invention provides a method for treating pathological lesions of the layers of the wall of the eye in which tissue destruction is effected by the laser radiation. In this way, glaucoma may be treated by effecting destruction of the ciliary body.

DESCRIPTION OF THE DRAWINGS

Methods in accordance with the invention will now be described with reference to the accompanying drawings, in which:

FIG. 5a) and b) shows ultrasonic transducer response on two different times scales;

DETAILED DESCRIPTION

The invention comprises a method for analysis and/or therapy of an eye comprising the step of directing laser radiation into the eye, the characteristics of the laser radiation being suitable to generate ultrasound at desired locations within the eye.

Figure 1:
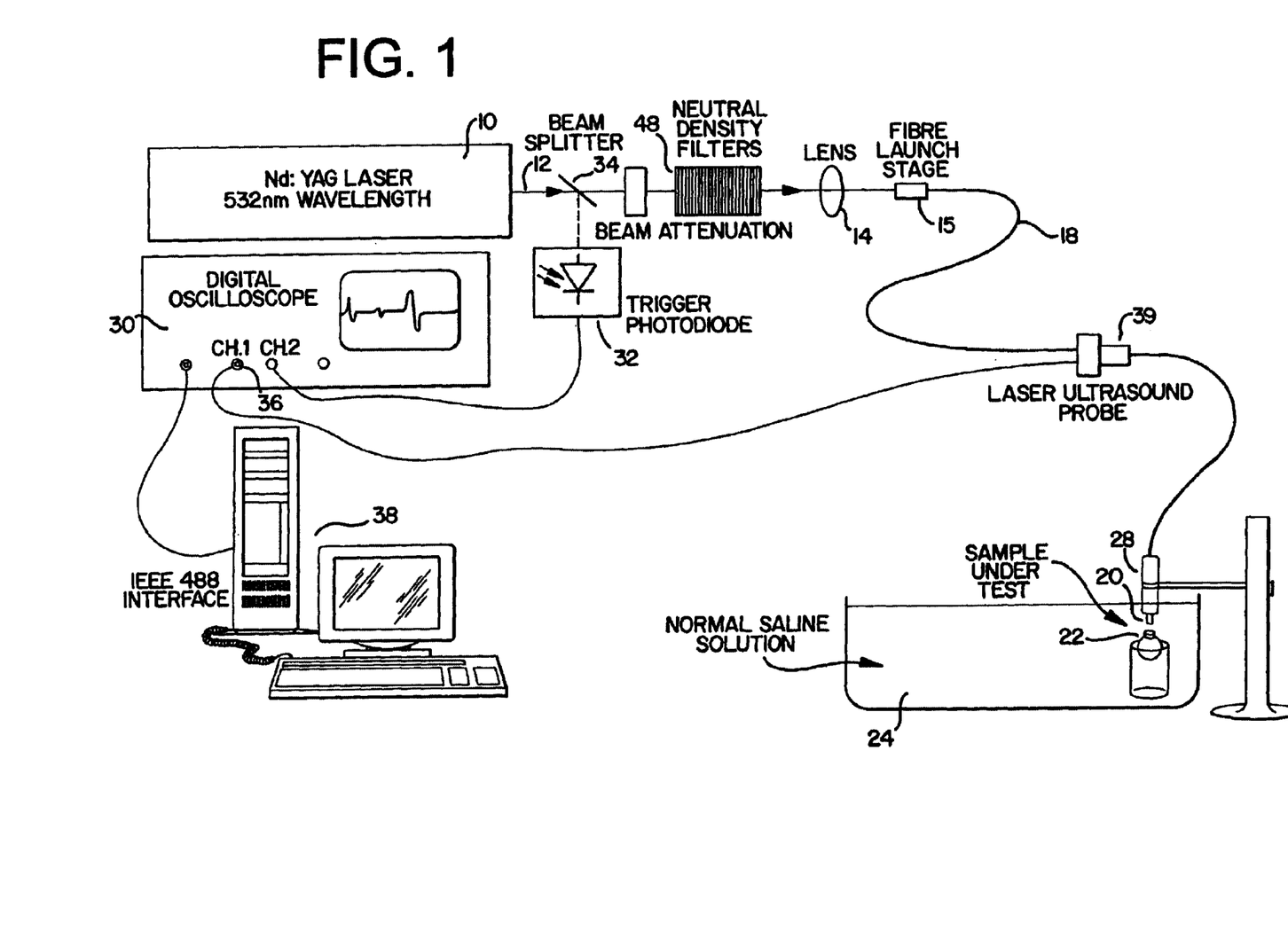
FIG. 1 is a schematic diagram of apparatus for analysing an eye.

FIG. 1 shows apparatus for performing the method, comprising a pulsed laser 10 producing a beam of laser radiation 12 which is focussed by a lens 14 into an optical connector 15 which is connected to an optical fibre 18. The laser beam 12 ultimately emerges from a source 20 which is one end of the optical fibre 18, this laser radiation then being directed into an eye 22 which is positioned in an acoustic coupling medium 24 such as a saline solution.

Figure 2:
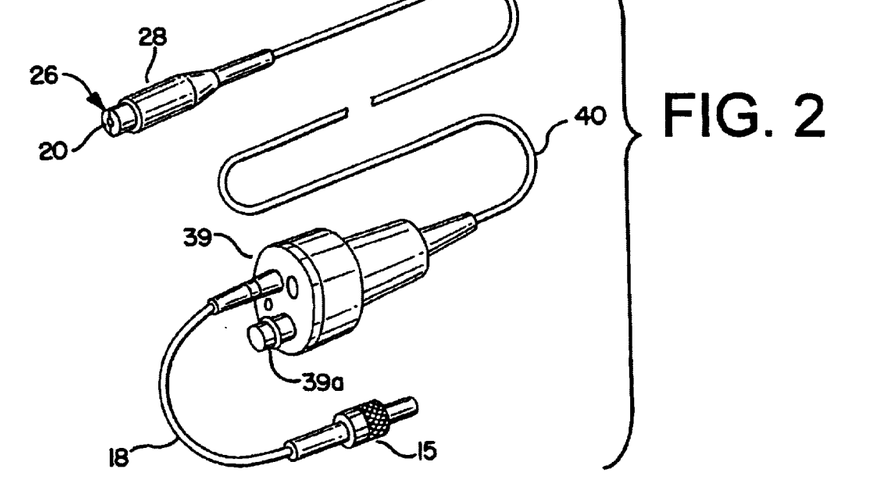
FIG. 2 shows the laser ultrasound sensor with housing.

As shown in FIG. 2, the source end 20 of the optical fibre 18 is mounted coaxially with ultrasonic transducer means 26 in a single housing 28.

Data are collected using a digital oscilloscope 30 (Tektronik TDS620A). The oscilloscope 30 is triggered by the output of a photodiode 32 (type BPX-65) which receives a small proportion of the laser radiation from a beam splitter 34. The output of the ultrasonic transducer means 26 is inputted to the oscilloscope 30 at socket 36. Data are transferred to a computer 38 equipped with National Instruments Lab Windows (RTM) software for further processing and analysis. For observing small amplitude features more clearly, two cascaded low-noise wideband amplifiers (Comlinear type CLC100) with a total gain of 40 db (not shown) were used for amplifying the transducer output signal.

Figure 3:
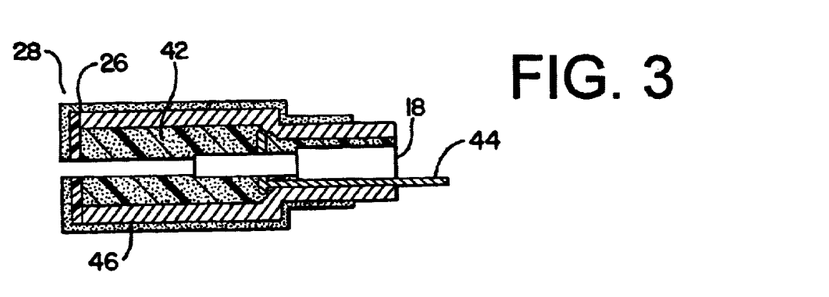
FIG. 3 is a cross sectional side view of the head of the probe.

FIG. 2 shows the portion of the apparatus comprising the optical fibre 18. Laser radiation is focussed into the optical fibre 18, which is of 600 $\mu$m OD, via a connector. The optical fibre 18 passes through a signal manifold 39 which comprises a connection 39a for electrical connection to the transducer means 26. A cable 40 runs between the manifold 39 and the housing 28, the cable 40 containing the optical fibre 18 and electrical signal leads from the housing 28. FIG. 3 shows the housing 28 in more detail. The housing 28 comprises a perspex shell, in which the ultrasonic transducer means 26 is located. Although the ultrasonic transducer means 26 might comprise a piezoelectric ceramic, it is preferred to use a piezoelectric polymeric material, preferably polyvinylidene fluoride (PVDF) or, most preferably, its copolymer with trifluoroethylene (TrFE). The PVDF is present on a film (Pennwalt Kynar film type 5028 NAD), the rear face of which is located on a conductive silver loaded epoxy support 42 (Circuit Works RTM, available from RS). The use of silver loaded epoxy is preferred because I) it exhibits advantageous mechanical properties of stiffness, acoustic impedance and good adhesion to PVDF and ii) it exhibits excellent electrical conductivity compared to conventional epoxy materials, resulting in increased detection sensitivity. A wire 44 makes electrical contact with the epoxy support 42, the main body of the wire 44 being located in cable 40. The housing 28 is coated with a silver loaded paint 46. The optical fibre 18 passes through the housing 28, preferably coaxially therewith.

Devices having ultrasonic transducer means and a source for directing laser radiation combined in a single housing are known from British Patent Application GB 2212920A and International Publication WO 94/28804. However, it should be noted that GB 2212920A is silent regarding the dimensions of such devices. Furthermore, WO 94/28804 is concerned with intravascular uses, and teaches that the outside diameter of the housing should be no greater than 3 mm. There is no such constraint when making measurements of the eye using laser induced ultrasound, and, indeed, housings of larger dimensions are desirable since the size of the ultrasonic transducer means can be increased, leading to greater sensitivity. Devices used to perform the method of the present invention preferably comprise housings (as defined above) having an outside diameter (or corresponding dimension, such as width) of greater than 3 mm, more preferably greater than 1 cm, most preferably greater than 2 cm.

Figure 4:
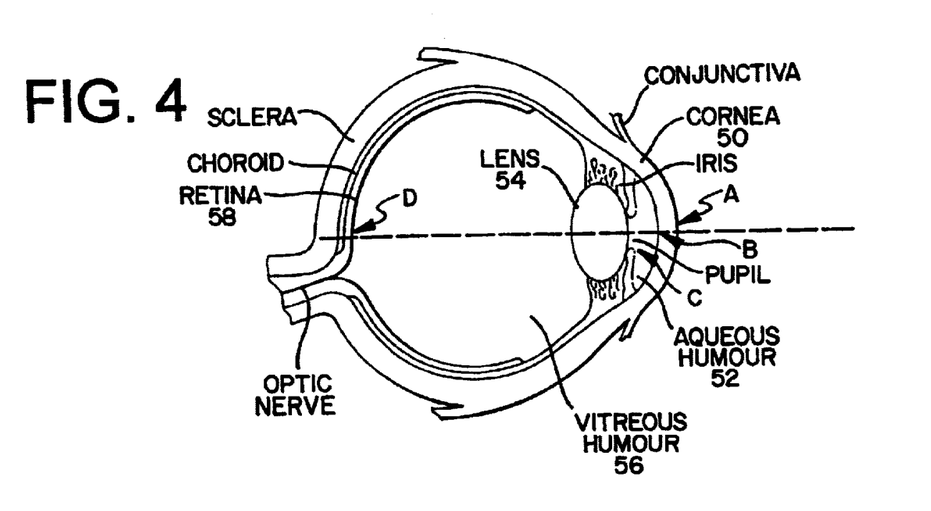
FIG. 4 is a first cross sectional side view of a human eye.

FIG. 4 shows a cross section through a human eye. Substantially identical structural components are present in the eye of other mammalian species. The eye produces images by focussing light onto the retina 58 with the lens 54. The passage of light from the front of the eye to the back of the eye involves the traversal of the cornea 50, aqueous humour 52, lens 54, and the vitreous humour 56, the light then impinging upon the retina 58.

Ultrasound is generated by absorption of light at an interface between two media which have different coefficients of absorption. The generation and detection of ultrasound in a complicated structure such as an eye, which has numerous interfaces between different structural components, is a complex process controlled by numerous parameters. In particular, it has not previously been possible to generate and detect ultrasound in the vitreous humour or at the retina/vitreous humour interface. The latter is required if knowledge of the overall dimension of the eye along the optical axis of the lens is desired. It is necessary to generate penetrating, low frequency ultrasound. The intensity of the light reaching these regions of the eye should be high enough to generate detectable ultrasound, but not so high as to cause damage to the eye. This intensity is affected by the absorption and scattering properties of the various components of the eye. Thus optical properties of the eye components at the wavelength of the laser radiation are important parameters. Pulse energy characteristics and the diameter of laser beam are also important parameters, since they determine the intensity of the laser radiation. It should be noted that if the laser radiation is not collimated, e.g., if it is focussed, the spot size of the laser beam will vary at different locations within the eye. For non-invasive measurements, the incident laser intensity will generally be sufficient to generate ultrasound by thermoelastic expansion of the interrogated tissue. Experiments were performed using the frequency doubled output of a Nd:YAG laser 10 (Quanta-Ray GCR-150) at 532 mm. The laser 10 is Q switched, producing pulses of 10 nsec duration at a repetition rate of 1.25 Hz with a pulse energy of 1.44 mJ. The laser beam passes through a number of neutral density filters 48 in order to attenuate the laser radiation so as to achieve an appropriate laser intensity incident on the eye under investigation. Absorption data for different eye components at 532 nm is shown in Table 1. In Table 2 is shown amplitude reflection coefficients at interfaces between layers in the eye. Amplitude reflection coefficients at the boundary between two consecutive layers are given by $$R = \frac{Z_1 - Z_2}{Z_1 + Z_2}$$

where $Z_1$ and $Z_2$ are the acoustic impedances of the first and second layers respectively.

TABLE 1

Some optical and acoustic properties of bovine eyeballs

| Structural Component | Percentage transmission[1] | Absorption Coefficient[3] (cm$^{-1}$) | Density[4] (Kg · m-3) | Ultrasound Velocity[4] (m · s$^{-1}$) | Acoustic Impedance (Rayl) |
|---|---|---|---|---|---|
| Cornea | 63% | 3.080 | 1076 | 1588 | 1708688 |
| Aqueous humour | 60% | 0.488 | 1003 | 1503 | 1507509 |
| Lens | 47% | 0.181 | 1071 | 1673 | 1791783 |
| Vitreous humour | 37% | 0.171 | 1009 | 1532 | 1545788 |
| Retina | 1%[2] | 36.106 | 1071[2] | 1532 | 1640772 |

[1]Percentage transmission through the eye reaching the anterior surface of a particular structure.
[2]Estimated values.
[3]These values were calculated using the Beer-Lambert Law.
[4]Average values are used.

TABLE 2

Amplitude reflection coefficients at the boundary between layers of bovine eyeball

| Type of interface | Amplitude reflection coefficient |
|---|---|
| Cornea/Aqueous humour | 6.26% |
| Aqueous humour/Lens | −8.62% |
| Lens/Vitreous humour | 7.37% |
| Vitreous humour/Retina | −2.98% |

It will be apparent to the skilled reader that other types of laser and other laser wavelengths may be utilised. Indeed, consideration of the parameters discussed above may suggest optimal wavelengths, spot sizes and pulse energies for the particular type of eye being examined.

Figure 5:
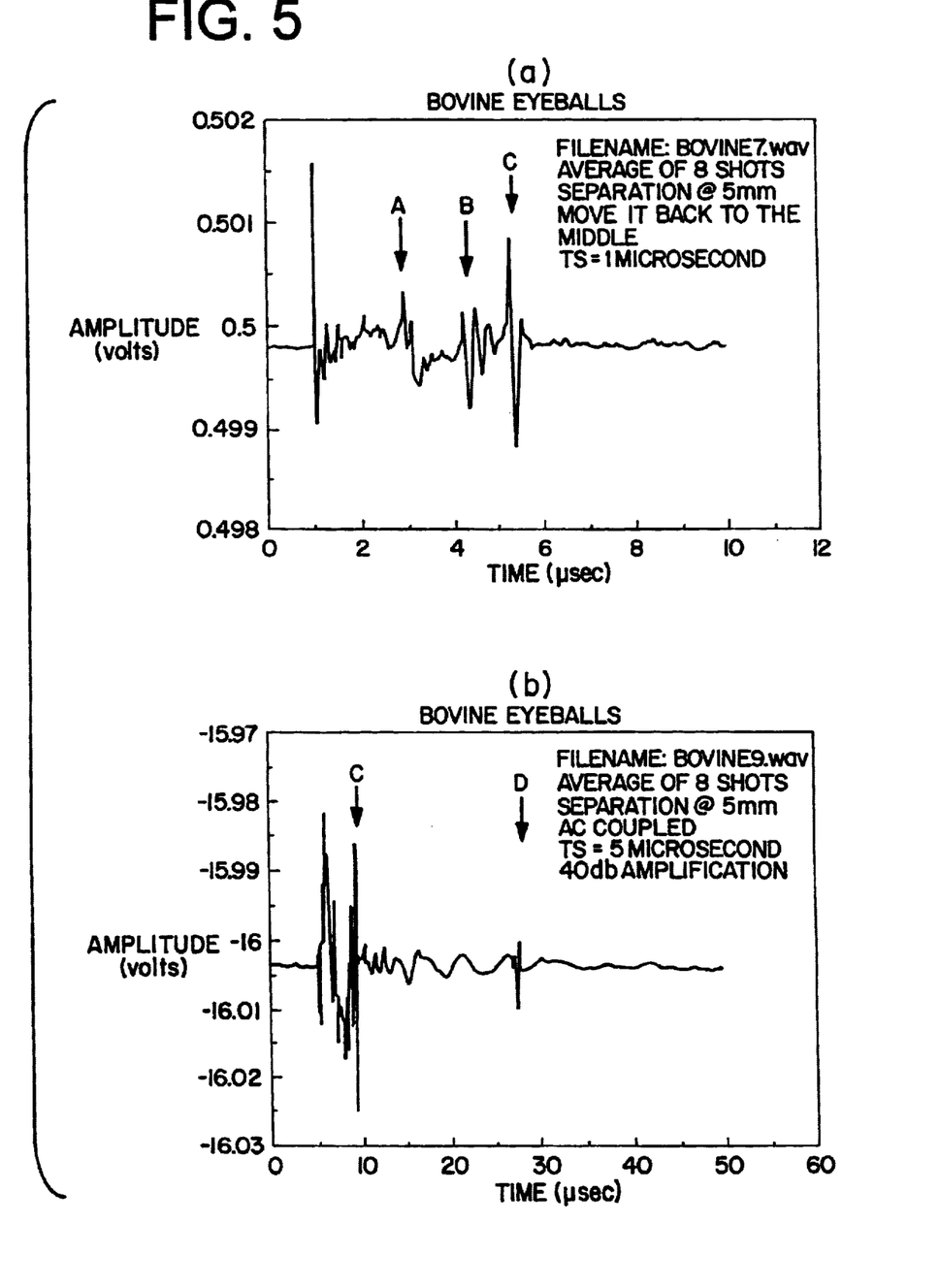

Measurements were made using laser radiation from the Nd:YAG laser to probe fresh bovine eyes, which were positioned in the saline solution 24. FIGS. 5a and 5b show the time resolved output of the PVDF film 26. Waveforms A, B, C, D are obtained showing bipolar transients characteristic of ultrasound pressure waves. Knowing the separation of the eye from the PVDF film 26 and the velocity of ultrasound through the various media, it is possible to calculate the depths of the interfaces producing waveform A, B, C, D. It is believed that waveform A corresponds to the saline solution/cornea interface. The other waveforms B, C, D correspond to depths of ca. 1.70 mm, 3.48 mm and 30.60 mm from the solution/cornea interface. These depths are expected if waveform B corresponds to the aqueous humour/cornea interface, C corresponds to the lens/aqueous humour interface and D corresponds to the retina/vitreous humour interface. These interfaces have been appropriately denoted A, B, C, D in FIG. 4. Thus the depth 30.60 mm associated with waveform D represents the overall dimension of the eye along the optical axis of the lens.

It should be noted that the waveform A may be attributable to more than one specific feature. Also there is no waveform readily attributable to the vitreous humour/lens interface, but this might be a sampling anomaly. Table 1 shows that the absorption coefficients of the vitreous humour and the lens are very similar at 532 mm, so difficulty in detecting associated ultrasound is perhaps not surprising. It is possible that there are larger differences in absorption properties of these components at different wavelengths, and thus this interface may be detectable using a different laser.

Figure 6:
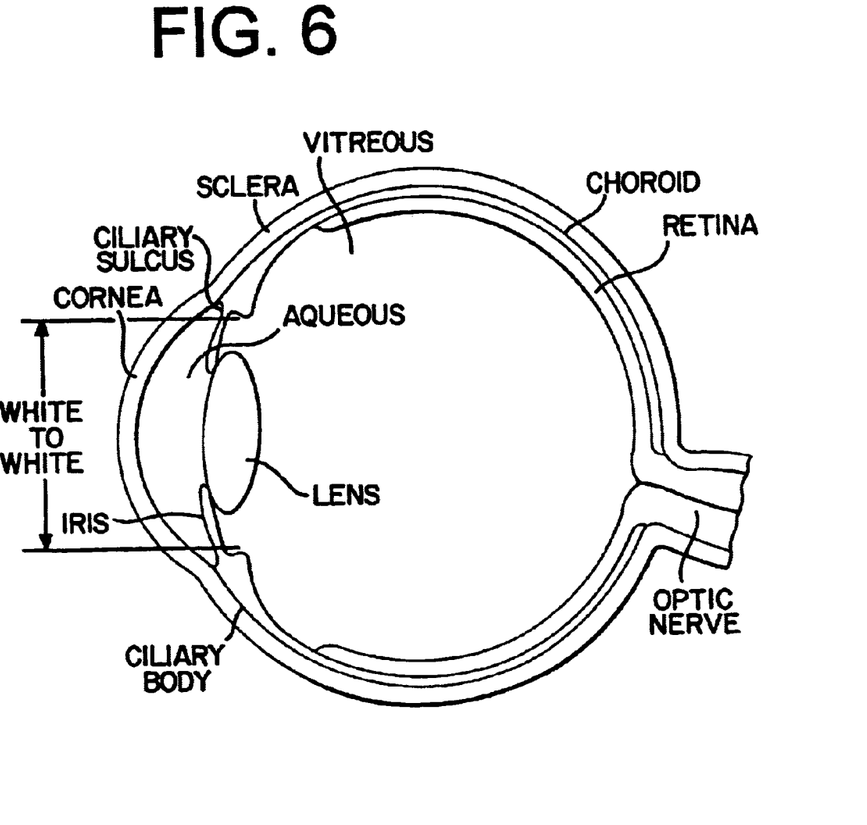
FIG. 6 is a second cross sectional side view of a human eye showing the White to White dimension.

There are numerous possible extensions to the technique. For example, White-White measurements can be made by directing the laser radiation into the eye substantially along an axis which is substantially non-parallel to the optical axis of the lens. The optical axis of the lens is shown as a broken line in FIG. 4. The White to White dimension is shown in FIG. 6.

In another variation, the point of entry of the laser radiation into the eye may be varied. This might be accomplished by translating the source, i.e., by moving the housing 28. By doing this, a whole eye B scan can be performed. Additionally, variation of the point of entry of laser radiation might be accomplished by tilting or otherwise pivoting the source. It is also possible to combine these two approaches, i.e., to traverse the point of entry of the laser radiation into the eye whilst making "off-axis" measurements, in order the provide additional information.

It is known that ultrasound focussing can be performed with synthetic aperture focussing techniques (SAFT). These techniques may be used for signal enhancement, or for scanning purposes. Prior art SAFT systems have utilised such focussing for generating and receiving ultrasound. Examples of publications disclosing SAFT, the contents of which are hereby incorporated by reference, are as follows: S R Doctor, T E Hall, and L D Reid, NDT International, 19 (1986) 163–167; M Krause, C Maierhofer and H Wiggenhauser, Proc. 6$^{th}$ Int. Conf. on Structural Faults and Repairs (London, UK), 1 (1995) 17–24; P W Lorraine, R A Hewes and D Drolet, Rev. of Progress in Quantitative Nondestructive Evaluation, 16 (1997) 555–562; E M Johansson and J E Mast, SPIE, 2275 (1994) 205–213; O T Von Ramm and S W Smith, IEEE Trans. Biomedical Engineering, BEM-30 (8), (1983) 438–452. It has been found that an adaption of SAFT methodologies can be advantageously used to perform ultrasound investigations of the eye. In the adaption, the SAFT methodology is used to receive ultrasound only (the ultrasound being generated by laser radiation using the principles described above).

Figure 7:
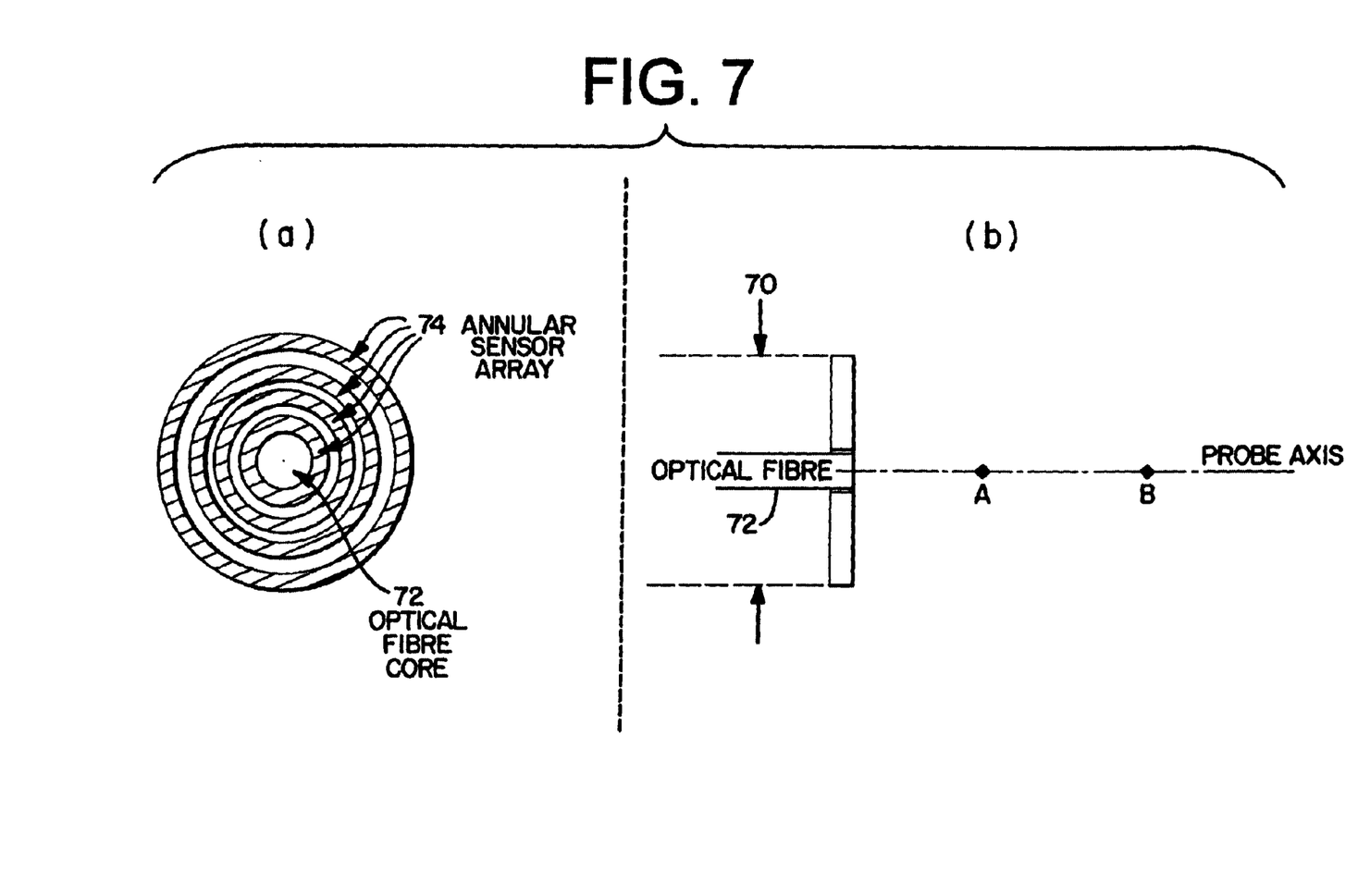
FIG. 7 shows a) a front view, and b) a side view of a probe head having annular sensors.
Figure 8:
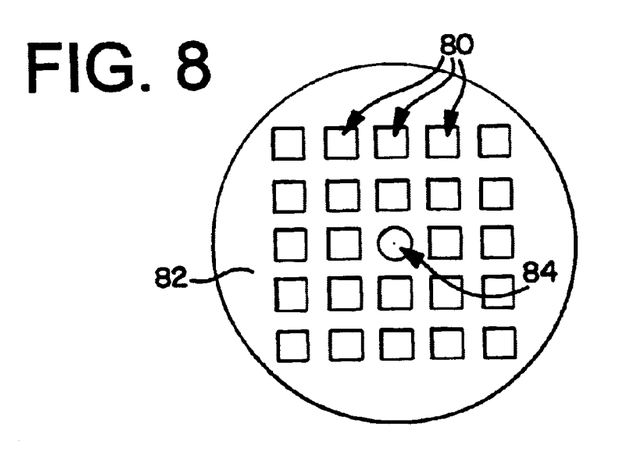
FIG. 8 shows a front view of a probe having a two dimensional array of sensors.

FIGS. 7 and 8 depict detector arrangements which employ SAFT methodology and which are advantageous in the extraction of images of the eye, or portions of the eye. A plurality of ultrasonic transducers are employed to provide a plurality of response waveforms, and the waveforms are processed by adding appropriate time delays thereto, so as to provide position sensitive measurements of the generated ultrasound. Advantageously, the transducers and the laser source are combined in a single housing or probe head, in a generally similar manner to that shown in FIGS. 1 to 3. FIG. 7 shows a housing 70 in which the laser emanates from an optical fibre core 72 which is surrounded by a plurality of substantially annular ultrasonic transducers 74 arranged substantially concentrically with respect to the optical fibre core 72.

Ultrasound returning to the transducers 74 is recorded, but in the signal processing of each transducer, time delays are added to each waveform to account for the delays of ultrasound reaching the transducers from, for example, point A. By using signal processing for synthetic apertures, a resultant signal amplitude for on-axis signals coming from point A may be produced. Then by suitable modification of the time delays for each transducer, signal amplitudes from other on axis positions may be calculated. In this way, digital signal processing can lead to signals emanating on axis from all points between A and B.

This probe provides enhanced on-axis signals, with improved spatial resolution. This probe, together with the signal processing, is only sensitive to on-axis signals. The probe head would then need to translate or pivot in an angular fashion in order to look at different regions of the eye. However, this arrangement can be advantageously used for single axis measurements due to the increased sensitivity achievable with this approach.

FIG. 8 shows a second end-face configuration. In this embodiment, there is an array of transducers 80 (FIG. 8 shows 34 sensors) in a housing 82. The array of transducers 80 is a two dimensional array with the optical fibre 84 from which the laser radiation emanates at the centre of the array. Once again, return ultrasound waveforms are recorded by the transducers 80 followed by signal processing using SAFT. For any one position in 3-D space in front of the probe, appropriate time-delays are added to each waveform to find calculated signal amplitude coming from that location. Re-calculations may then be performed for other locations in space, so that a complete 3-D picture emerges. In this way, imaging of the eye, or portions of the eye, can be achieved. Both techniques are intensive in computer memory for digital calculations, but this is not likely to be restrictive with the speed of modern computer systems. It should be noted that with a 600 $\mu$m optical fibre (used to perform the experiments described above) the emergent laser beam has a half angle divergence of 30°. Thus, laser radiation emerging from a fixed position optical fibre is capable of illuminating a significant volume of the eye. It is possible to modify the optical fibre tip in order to provide more divergence, or to employ a different optical system which produces a divergent beam. Alternatively, the point of entry of laser radiation into the eye might be varied.

The outside diameter of the housing can be as little as 1–2 mm, although the dimensions can be as large as 10 mm or even greater. It should be noted that it is not a necessary condition that the optical fibre 84 in FIG. 8 is positioned centrally with respect to the transducer array. Additionally, it should be noted that it is possible to use more than one optical fibre: indeed, an array of optical fibres might be provided. This represents another way in which variation of the point of entry of laser radiation into the eye can be achieved, and might be used with the multiple transducer SAFT approach or with a single ultrasonic transducer.

It may be possible to derive information concerning light scattering sources present in the eye from the generated ultrasound. Indeed, it is possible that some of the additional features present in the data shown in FIGS. 5a and 5b are caused by ultrasound generated at such scattering sources, although this has not been confirmed. Alternatively, information may be obtained by comparing the intensities and/or shapes of the waveforms associated with the generation of ultrasound at specific interfaces. Measurements of scattering sources might provide information on the opacity of the lens or the presence of flare and cells and like scattering sources in the vitreous humour and/or the aqueous humour.

Another application area is the investigation of cataracts. In the clinical practice of ophthalmology, there are two areas where subjective assessment is not parallelled by objective measurement. The two situations are: (a) the progressive formation of cataract and (b) the progressive formation of secondary cataract. In the former situation, the crystalline lens undergoes discolouration during its life span, with associated hardening of the nucleus and variable degree of pacification. Indication for surgery depends on assessment of cataract condition. Once the lens has been removed and replaced with a lens implant, the crystalline lens capsule is retained as the envelope in which the new lens is clasped, more or less acting as a shrink wrap or cling film effect. Due to a variety of pathological processes, including migration of cells and changes in their character, the posterior lens capsulate may undergo fibrosis or other causes of pacification. In other words, the patient develops a secondary cataract. In both cases, objective assessment of the degree of pacification is required.

Figure 9:
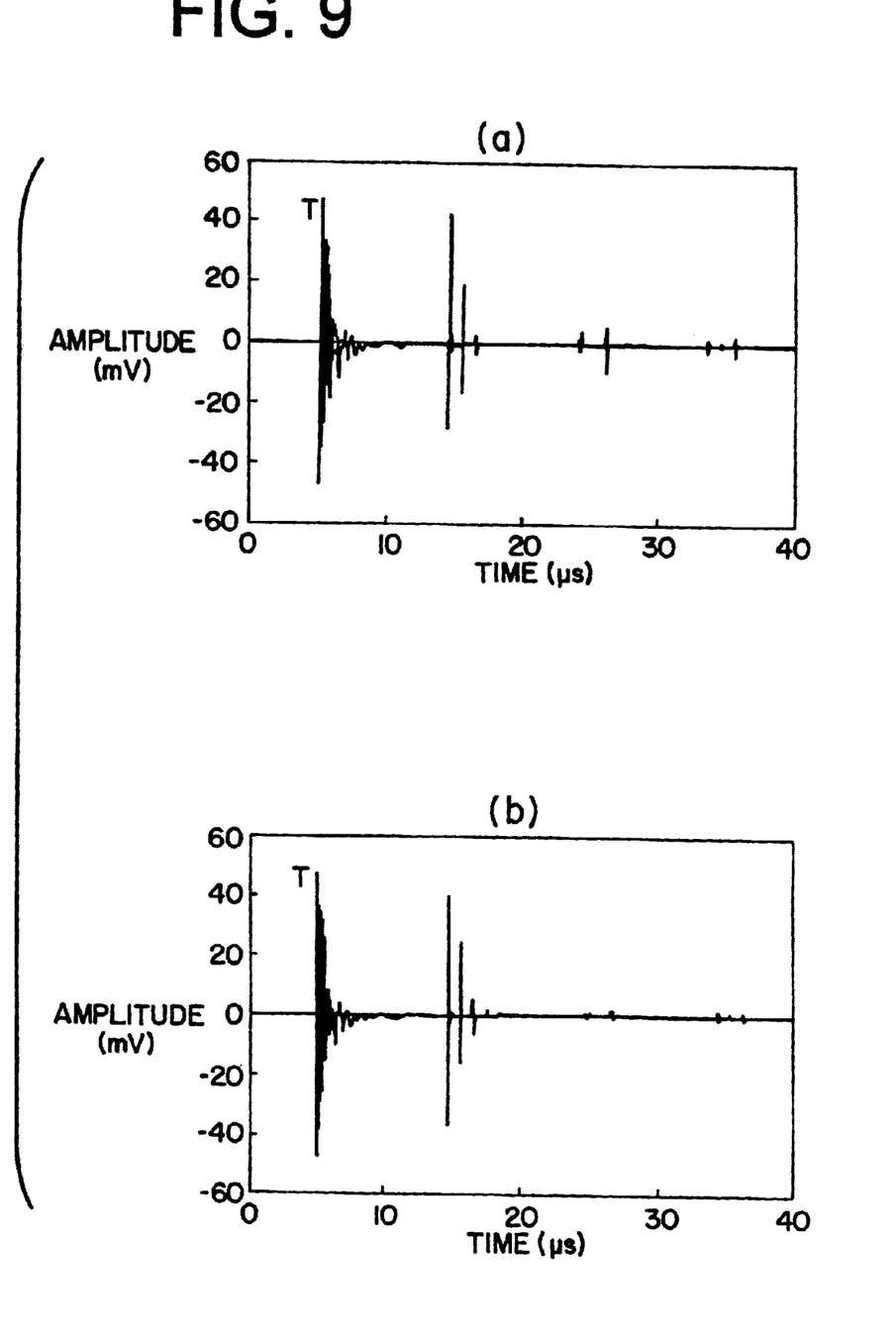
FIG. 9 shows ultrasonic response from a plastic lens a) when transparent and b) when translucent.

Experiments have been performed using laser-generated ultrasound measurements for the assessment of cataract formation in which a plastic lens is held in a normal saline solution similar to the set-up shown in FIG. 1. Initially, the lens was examined in its normal transparent state. The surface of the rear of the lens was then roughened using fine emery paper until it became translucent. Measurements were then repeated on the modified lens. The two sets of signals are shown in FIG. 9. There are clear differences in the amplitudes of the two signals recorded for the translucent lens compared with the transparent one. Interestingly, the reduction in thickness caused by the abrasion of the rear surface also shows up in the timing differences for the two ultrasonic signals. These experiments indicate that laser generated ultrasound may have utility in the assessment of cataracts.

It is also possible that the present method might be used for therapeutic purposes. In particular, it may be possible to use laser radiation to affect local tissue destruction, for example of the ciliary body as a treatment for glaucoma. The aim is to reduce the secretion of aqueous humour from the ciliary body and thus reduce the elevated intraocular pressure which is associated with advanced glaucoma. It is understood that tissue destruction would be achieved by local heating caused by the laser irradiation, and not by ultrasound, which will be generated as a by-product of the treatment. However, it is likely that detection of the generated ultrasound will be desirable so as to monitor the course of treatment. It is possible that higher laser intensities, causing ultrasound emission in the ablation regime, might be utilised. Alternatively, it is possible to utilise two separate lasers, possibly with laser radiation from both lasers propagating along the same optical axis. The first laser might operate at a relatively high laser intensity, for therapeutic purposes, causing the destruction of cells. Either simultaneously or sequentially, a second laser might be used for diagnostic purposes, monitoring the zone of therapy, or other zones within the eye. In a sequential scheme, the two lasers might operate at a common pulse repetition frequency, but with an appropriate delay between pulses from the two lasers. It is also possible for the two lasers to operate at different pulse repetition frequencies. A further possibility is to use a single laser, but to split the beam into a strong beam and a weak beam.

A technique currently used to treat glaucoma is to ablate the ciliary body from outside with a diode laser. This is placed a standard distance (about 1 mm) behind the edge of the cornea on the white of the eye and the laser radiation is applied for a few seconds. Because of anatomical variations, there is currently no way of determining if the laser radiation is correctly aligned with respect to the ciliary body, or of assessing how much damage has been done by the treatment. The method of the present invention might be very usefully combined with such prior art techniques to provide structural information and/or information on the alignment of the therapeutic laser beam. A two laser scheme would be employed. Information could be provided using ultrasound before, after or possibly even during the ablation.

The techniques described above with reference to glaucoma might be used to destroy other localised lesions of the inner aspect of the wall of the eye such as angiomas or certain malignant tumours.

In the present example the acoustic coupling medium is a saline solution. Other media are within the scope of this invention, including gels, and indeed it is possible that such media might prove more comfortable to subjects undergoing examination using the present invention.

What is claimed is:

1. A method for analysis of an eye comprising the steps of:
   directing laser radiation into the eye, the characteristics of the laser radiation being suitable to generate ultrasound at desired locations within the eye;
   measuring the time taken for the generated ultrasound to propagate from the location at which it is generated to an ultrasonic transducer means, or a time value closely related thereto, and deriving therefrom the spatial dimensions of the eye or one or more components of the eye.

2. A method according to claim 1 directing such that ultrasound is generated at or in the vitreous humor or the retina.

3. A method according to claim 2, further comprising the step of detecting the generated ultrasound by ultrasonic transducer means connected to the eye by an acoustic coupling medium.

4. A method according to claim 3, in which the acoustic coupling medium comprises a saline solution.

5. A method according to claim 3, in which the acoustic coupling medium comprises a gel.

6. A method according to claim 1, in which the laser radiation is directed into the eye substantially along an axis which is substantially parallel to the optical axis of the lens.

7. A method according to claim 1, in which the laser radiation is directed into the eye substantially along an axis which is substantially non-parallel to the optical axis of the lens.

8. A method according to claim 1, in which the point of entry of the laser radiation into the eye is varied.

9. A method according to claim 8, further comprising the step of constructing an image of the eye or one or more components of the eye from measurements made at a plurality of points of entry of the laser radiation into the eye.

10. A method according to claim 1, in which a plurality of ultrasonic transducers are employed to provide a plurality of response waveforms, and the waveforms are processed by adding appropriate time delays thereto so as to provide position sensitive measurements of the generated ultrasound.

11. A method according to claim 10, in which the laser radiation emanates from a source, and the plurality of ultrasonic transducers comprise a plurality of substantially annular transducers arranged substantially concentrically with respect to the source.

12. A method according to claim 10, in which the plurality of ultrasonic transducers, and the response waveforms provided thereby, are processed to provide a three-dimensional image of the eye or of one or more components of the eye.

13. A method according to claim 1, further comprising the step of deriving information concerning the lens from the generated ultrasound.

14. A method according to claim 1, further comprising the step of deriving information concerning light-scattering sources present in the eye from the generated ultrasound.

15. A method according to claim 14, further comprising the step of measuring the opacity of the lens.

16. A method according to claim 14, further comprising the step of detecting the presence of flare and cells and light scattering sources in the vitreous humor and/or the aqueous humor.

17. A method according to claim 14, a device having ultrasonic transducer means and a source for directing laser radiation to the eye combined in a single housing is used in the detecting and measuring steps.

18. A method for performing combined analysis and therapy of an eye comprising the steps of:
   directing therapeutic laser radiation into the eye, the characteristics of the ultrasound generating laser radiation being suitable to effect a therapeutic treatment of the eye;
   directing ultrasound generating laser radiation into the eye, the characteristics of the ultrasound generating laser radiation being suitable to generate ultrasound at desired locations within the eye; and,
   analyzing the generated ultrasound in order to derive information concerning the eye or the alignment of the therapeutic laser radiation with respect to the eye.

19. A method according to claim 18 in which a single laser is used in the therapeutic and ultrasound generating step.

20. A method according to claim 18 in which separate lasers are used in the therapeutic and ultrasound generating steps.

21. A method according to claim 18 in which the therapeutic and ultrasound generating laser directing steps are practiced such that the therapeutic laser radiation and the ultrasound generating laser radiation propagate along the same optical axis.

22. A method according to claim 18 in which a sufficient amount of the therapeutic laser radiation is directed so as to effect tissue destruction so as to treat pathological lesions of the layers of the wall of the eye.

23. A method according to claim 18 in which a sufficient amount of the therapeutic laser radiation is directed so as to effect destruction of the ciliary body so as to treat glaucoma.

24. A method according to claim 18, in which a sufficient amount of ultrasound is generated at or in the vitreous humour or the retina.

25. A method according to claim 18 further comprising the step of detecting the generated ultrasound by ultrasonic transducer means connected to the eye by an acoustic coupling medium.

26. A method for analysis of an eye according to claim 25, in which the analyzing step includes measuring the time taken for the generated ultrasound to propagate from the location at which it is generated to the ultrasonic transducer means, or a time value closely related thereto, and deriving information concerning the eye therefrom.

27. A method according to claim 26, in which the analyzing step is practiced to acquire information concerning the eye including the spatial dimensions of the eye or of one or more components of the eye.

* * * * *